United States Patent [19]

Morley

[11] Patent Number: 4,476,117

[45] Date of Patent: Oct. 9, 1984

[54] DIMERS OF PEPTIDE AMIDES

[75] Inventor: John S. Morley, Cheadle Hulme, England

[73] Assignee: Imperial Chemical Industries PLC, London, England

[21] Appl. No.: 449,880

[22] Filed: Dec. 15, 1982

[30] Foreign Application Priority Data

Jan. 12, 1982 [GB] United Kingdom ................ 8200859

[51] Int. Cl.³ .................... C07C 103/52; A61K 37/02
[52] U.S. Cl. .............................. 424/177; 260/112.5 R
[58] Field of Search .................. 260/112.5 R; 424/177

[56] References Cited

U.S. PATENT DOCUMENTS

| | | | |
|---|---|---|---|
| 4,221,682 | 9/1980 | Sarantakis .................... | 260/112.5 R |
| 4,309,343 | 1/1982 | Gesellchen .................. | 260/112.5 E |
| 4,320,051 | 3/1982 | Sarantakis .................... | 260/112.5 R |
| 4,322,342 | 3/1982 | Smithwick, Jr. et al. ... | 260/112.5 R |
| 4,331,593 | 5/1982 | Smithwick, Jr. et al. ... | 260/112.5 R |

OTHER PUBLICATIONS

*Chemical Abstracts*, 97, 84 (1982), Abst. No. 97:174912s.
*Chemical Abstracts*, 97, 171 (1982), Abst. No. 97:175692g.
Costa et al., (Abstract, 7th American Peptide Symposium, Madison, Wisconsin, U.S.A., Jun. 14–19, 1981).
Lipkowski and Konecka (Abstract, Peptides and their Receptors in the Central Nervous System, Hungarian and Polish Pharmacological Societies, 5th Joint Symposium, Zakopane, Poland, Oct. 3–4, 1981).
Hahn et al., Research Communications in Chemical Pathology and Pharmacology, 1977, 18 (1), pp. 1–9.

*Primary Examiner*—Delbert R. Phillips
*Assistant Examiner*—F. Moezie
*Attorney, Agent, or Firm*—Cushman, Darby & Cushman

[57] ABSTRACT

Compounds of the formula:

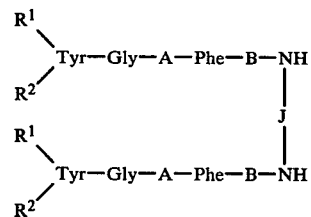

wherein $R^1$ and $R^2$ stand for alk-2-enyl radicals of not more than 6 carbon atoms, A stands for Gly or Azgly, B stands for Leu or Met, J stands for —$(CH_2)_n$—, wherein n stands for an integer from 1 to 10, or a phenylene radical, and pharmaceutically-acceptable acid-addition salts thereof. Processes for the manufacture of the compounds. Pharmaceutical compositions comprising one of the compounds and a pharmaceutical diluent or carrier. The compounds are selective δ-opiate-receptor antagonists.

8 Claims, No Drawings

DIMERS OF PEPTIDE AMIDES

This invention relates to dimers of peptide amides which are active as antagonists at the so-called opiate receptors in warm-blooded animals.

It is generally recognised that in warm-blooded animals there are at least two distinct types of opiate receptor, i.e., the μ-receptor and the δ-receptor (see Robson & Kosterlitz, Proc. R. Soc. London.(B), 1979, 205, 425–432, Goodman et al., Proc. Natl. Acad. Sci. U.S.A., 1980, 77, 6239–6243, and Simon, Trends in Pharmacol. Sci., 1981, 2, 155). Compounds are known, for example naloxone, which are antagonists of natural endogenous agonist substances, for example enkephalins, at opiate receptors. However, all of these known antagonists are more potent at the μ-receptors than at the δ-receptors. That is, all of the known opiate antagonists are selective μ-receptor antagonists. In contrast, the compounds of this invention are more potent at the δ-receptors than they are at the μ-receptors. Thus, the compounds of this invention are selective δ-receptor antagonists.

Costa et al. (Abstract, 7th American Peptide Symposium, Madison, Wis., U.S.A., June 14–19, 1981) have described the preparation of cross-linked dimers of D-Ala²-enkephalin amide of the formula:

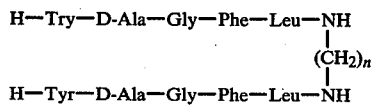

in which n stands for 2, 4, 6, 8, 10 or 12 (see below as regards the abbreviations used for the amino acids). The compounds were evaluated for receptor-binding activity using [³H]-[D-Ala², Met⁵]-enkephalin amide as a tracer, [D-Ala², Leu⁵]-enkephalin amide as a standard, and rat brain membranes in the presence of bacitracin at 25° C. The dimers exhibited increased affinity for opiate δ-binding sites as compared with the standard, the most potent (in which n stands for 2) being twice as potent as the standard.

Lipkowski and Konecka (Abstract, Peptides and their Receptors in the Central Nervous System, Hungarian and Polish Pharmacological Societies 5th Joint Symposium, Zakopane, Poland, Oct. 3–4, 1981) have described the preparation of cross-linked dimers of tetrapeptides of the formula:

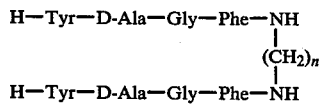

in which n stands for 0 or 3. The compounds are opiate receptor agonists. Guinea pig ileum (GPI) and mouse hot plate (MHP) tests showed the high dependency of biological activity on the value of n. The compound in which n stands for 3 exhibited activity in the GPI test related to that of the standard, [D-Ala², Met⁵]-enkephalin amide, but no activity in the MHP test. The compound in which n stands for 0 exhibited ten times the activity of [D-Ala², Met⁵]-enkephalin amide in the GPI test, and high activity (related to that of morphine) in the MHP test.

In U.S. Pat. No. 4,309,343 there are described and claimed compounds of the formula:

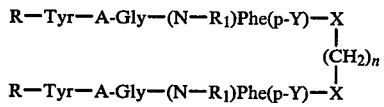

in which

R stands for hydrogen or a methyl radical,

A stands for the residue of a D-amino acid selected from D-Ala, D-Abu, D-Ser, D-Thr and D-Met, $R_1$ stands for hydrogen or a $C_{1-3}$ primary alkyl, cyclopropylmethyl or allyl radical, Y stands for hydrogen or a fluorine atom, n stands for an integer from 1 to 10, and X stands for —NH— or a group of the formula:

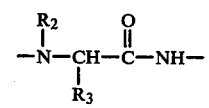

in which $R_2$ stands for hydrogen or a $C_{1-3}$ primary alkyl radical, $R_3$ stands for a phenyl, 2-methylthioethyl or isobutyl radical, or $R_2$ and $R_3$ taken together stand for —(CH$_2$)$_3$—; provided that, when $R_2$ is other than hydrogen, $R_1$ stands for hydrogen. It is stated in the specification that the compounds exhibit analgesic activity and also neuroleptic activity. It is also stated that the stereoconfiguration of the compounds is an essential feature. Thus, the chirality of the amino acid residues, reading from position 1 to position 4 for the tetrapeptide and pentapeptide derivatives is L, D, none, and L.

According to the present invention there are provided compounds of the formula:

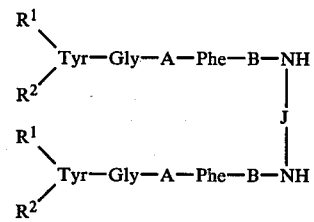

wherein $R^1$ and $R^2$, which may be the same or different, stand for an alk-2-enyl radical of not more than 6 carbon atoms, A stands for Gly or Azgly, B stands for Leu or Met, and J stands for a group of the formula —(CH$_2$)$_n$—, wherein n stands for an integer from 1 to 10, or for a phenylene radical, and pharmaceutically-acceptable acid-addition salts thereof.

It is to be understood that, in the compounds of this invention, $R^1$ and $R^2$ are linked to the nitrogen atom of Tyr. It is also to be understood that throughout this specification the abbreviations used for amino acids are standard abbreviations used in the art. Azgly stands for glycine in which the α-CH has been replaced by a nitrogen atom. When the configuration of an amino acid is not designated herein, it is to be understood that it has the natural L configuration (except, of course, for Gly and Azgly, which have no chiral centre).

$R^1$ and $R^2$ may, for example, stand for an allyl or crotonyl radical. n may, for example, stand for 2, 4, 6 or 8. When J stands for a phenylene radical it may, for example, be an o-phenylene radical.

Preferred compounds of the invention are [diallyl-Tyr-Gly-Gly-Phe-Leu-NH-CH$_2$-]$_2$ and [diallyl-Tyr-Gly-Azgly-Phe-Leu-NH-CH$_2$-]$_2$.

The salts of the invention are derived from an inorganic or organic acid which affords a pharmaceutically-acceptable anion, for example hydrochloric, phosphoric, acetic, citric or trifluoroacetic acid.

The compounds of the invention may be manufactured by processes which are known in themselves for the manufacture of chemically analogous compounds.

According to a further feature of the invention there is provided a process for manufacturing the compounds of the formula V and pharmaceutically-acceptable acid-addition salts thereof, which comprises reacting a protected compound of the formula:

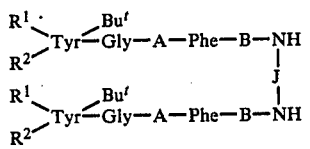

wherein Bu$^t$ stands for a t-butyl radical which in the form of the p-t-butoxy radical, protects the p-hydroxy radical in Tyr, with hydrogen chloride or trifluoroacetic acid, and wherein R$^1$, R$^2$, A, B and J have the meanings stated above.

Hydrogen chloride may be used in the form of an aqueous solution thereof, for example at a concentration between N— and that of a saturated solution, or it may be used as a solution in an organic solvent, for example ethyl acetate, methanol, acetic acid, diethyl ether or dioxan, or a mixture of any of these. The concentration used may be any concentration up to saturation, and is preferably in the range 2N to 6N. The reaction is preferably carried out at a temperature between 0° C. and ambient temperature, and optionally in the presence of a scavenger, for example anisole, methionine or dimethyl sulphide.

Trifluoroacetic acid may be used in the absence of any additional diluent or solvent, or it may be diluted with 5–10% by volume of water. The reaction is preferably carried out at ambient temperature, and optionally in the presence of a scavenger, for example 2-mercaptoethanol or anisole.

The protected bis-peptide-amides used as starting materials in the process of the invention are obtainable by conventional procedures for preparing analogous mono-peptide derivatives, starting from a diamino compound of the formula H$_2$N-J-NH$_2$, wherein J has the meaning stated above. Similarly, the pharmaceutically-acceptable acid-addition salts of the invention are obtainable by conventional procedures.

The activity of the compounds of the invention as antagonists at opiate receptors has been demonstrated in the guinea pig ileum test ("ileum test") and the mouse vas deferens test ("vas test"); see the article by Shaw et al. in "Characteristics and Function of Opioids", edited by Van Ree and Terenius, Elsevier/North-Holland Biomedical Press, 1978, 185-195. It is generally recognised that in the guinea pig ileum the μ-type of opiate receptor predominates, and that in the mouse vas deferens the δ-type of opiate receptor predominates. The potency of a compound in the above-mentioned tests is expressed as a Ke value, i.e. the concentration of the compound (antagonist) in the presence of which the agonist concentration has to be doubled in order to maintain a constant response. [Leu]-enkephalin is used as the agonist in both tests. The potency of any particular compound in the tests depends upon its precise chemical structure, but the compounds of the invention are active in the ileum test at a concentration in the range 300 nM to 30M, and in the vas test at a concentration in the range 1 nM to 1 μM (μM stands for micromolar, i.e. 10$^{-6}$ mole per liter, and nM stands for nanomolar, i.e. 10$^{-9}$ mole per liter).

As an indication of the lack of toxicity of a specific compound of the invention, namely [diallyl-Tyr-Gly-Gly-Phe-Leu-NH-CH$_2$-]$_2$, that compound is tolerated in the rat at a subcutaneous dose of at least 15 mg./kg.

Because of their activity as opiate receptor antagonists, the compounds of the invention may be used for the treatment of the following conditions and/or diseases in man: schizophrenia and other mental illnesses, neurological deficit resulting from physical or metabolic trauma, for example stroke or stress, or shock, anorexia nervosa, epilepsy, disorders of the endocrine function including post-menopausal flushing, or gastro-intestinal disorders. The compounds may also be used as sedatives, or as an adjunct to opiate analgesic therapy. When a compound of the invention is used for the treatment of man, it may be administered orally, or parenterally, for example by intravenous, subcutaneous or intramuscular injection or by infusion, or nasally, sublingually or rectally. A recommended daily oral dose for man is in the range 100 μg. to 500 mg. Such a dose may be administered as a single daily dose or it may be divided into, for example, three doses per day. A recommended parenteral dose for man is 100 μg. to 250 mg., a recommended nasal dose is 1 mg. to 100 mg., a recommended sub-lingual dose is 100 μg. to 250 mg., and a recommended rectal dose is 200 μg. to 500 mg.

The compounds of the invention may also be used as research tools or diagnostic agents in pharmacological or related studies.

According to a further feature of the invention there are provided pharmaceutical compositions comprising a compound of the formula V, wherein R$^1$, R$^2$, A, B and J have the meanings stated above, or a pharmaceutically-acceptable acid-addition salt thereof, and a pharmaceutically-acceptable diluent or carrier.

The pharmaceutical compositions of the invention may be in a form suitable for oral, parenteral, nasal, sub-lingual or rectal administration. Thus, for example, they may be in an orally-administrable unit dosage form, for example tablets or capsules, which may optionally be adapted for sustained or controlled release, or they may be in an injectable form, for example a sterile injectable solution or suspension, or in the form of a nasal spray or a suppository. All of the pharmaceutical compositions of the invention are obtainable in conventional manner using conventional diluents or carriers.

The pharmaceutical compositions of the invention may optionally contain, in addition to a compound of the invention:
(1) a known opiate antagonist, for example naloxone;
(2) a known psychotropic agent, for example an antipsychotic agent, for example chlorpromazine, or an antidepressant agent, for example imipramine, or an anxiolytic agent, for example chlordiazepoxide;
(3) a known analgesic agent, for example morphine; or
(4) a known anticonvulsant agent, for example primidone.

The invention is illustrated but not limited by the following Examples in which the temperatures are expressed in degrees Celsius, the expression "in vacuo" signifies that the pressure used was approximately 12 mm., and the $R_f$ values refer to ascending thin layer chromatography on silica gel plates (Kieselgel G). The solvent systems used were as follows (the ratios are by volume):

$R_fA$ n-butanol/acetic acid/water (4:1:5)
$R_fB$ n-butanol/acetic acid/water/pyridine (15:3:12:10)
$R_fC$ s-butanol/3% w/v aqueous ammonium hydroxide (3:1)
$R_fD$ acetonitrile/water (3:1)
$R_fH$ cyclohexane/ethyl acetate/methanol (1:1:1)
$R_fK$ chloroform/methanol/water (55:40:10)
$R_fP$ chloroform/methanol (19:1)
$R_fQ$ chloroform/methanol (9:1)

The following abbreviations are used in this specification:
BOC—t-butoxycarbonyl
$Bu^t$—t-butyl
DCCI—dicyclohexylcarbodiimide
DMF—dimethylformamide
ME—methyl
mM—millimole
NMR—nuclear magnetic resonance
TFA—trifluoroacetic acid
Z—benzyloxycarbonyl

EXAMPLE 1

[Diallyl-Tyr(Bu$^t$)-Gly-Gly-Phe-Leu-NH-CH$_2$-]$_2$ (0.85 g., 0.61 mM) was dissolved in TFA/water 9:1 v/v (20 ml.). The solution was kept at ambient temperature for one hour. The excess reagent was then evaporated in vacuo and the residue was dried in vacuo over potassium hydroxide. Trituration of the residue was diethyl ether gave a white solid which was collected by filtration and washed with diethyl ether. There was thus obtained (diallyl-Tyr-Gly-Gly-Phe-Leu-NH-CH$_2$-)$_2$ bis-trifluoroacetate, having $R_fA$ 0.63, $R_fB$ 0.91, $R_fC$ 0.77, $R_fH$ 0.7, $R_fK$ 0.9 and $R_fQ$ 0.19. The structure was confirmed by NMR.

The compound used as the starting material in the procedure described above was obtained as follows:

A. (H-Phe-Leu-NH-CH$_2$-)$_2$.2HCl

Z-Phe-Leu-OH (9.25 g., 20 mM), 1-hydroxybenzotriazole (2.7 g., 20 mM) and 1,2-diaminoethane (0.66 ml., 10 mM) were dissolved in DMF (30 ml.) and the solution was cooled to 0°. DCCI (4.12 g., 20 mM) was added and the mixture was stirred at 0° for 1 hr. and then at ambient temperature for 18 hr. The solid reaction mixture was stirred together with 2N-aqueous potassium bicarbonate (100 ml.) for 5 min., and the mixture was then filtered to give, as the solid residue, a mixture of dicyclohexylurea and (Z-Phe-Leu-NH-CH$_2$-)$_2$. The said mixture was dissolved in glacial acetic acid (700 ml.), and a mixture of 5% palladium-on-carbon catalyst (1.6 g.) and water (50 ml.) was added. The mixture was vigorously stirred and a slow stream of hydrogen was bubbled through it at ambient temperature for 16 hr. The catalyst was filtered off (kieselguhr) and washed with acetic acid (50 ml.). The filtrate and washings were combined, and the solvent was evaporated in vacuo. The residue was partially dissolved in water (200 ml.) at ambient temperature. The insoluble solid (mostly dicyclohexylurea from the previous step) was filtered off. 10N-Hydrochloric acid (2.5 ml.) was added to the filtrate, the mixture was evaporated in vacuo, and the solid which precipitated, (H-Phe-Leu-NH-CH$_2$-)$_2$ dihydrochloride, was collected by filtration and washed with diethyl ether (4×20 ml.).

B. Diallyl-Tyr(Bu$^t$)-Gly-Gly-OH

Diallyl-Tyr(Bu$^t$)-OH (5.0 g., 15.75 mM.) was dissolved in DMF (50 ml.) and the solution was cooled to −10°. N-Methylmorpholine (1.73 ml., 1 equivalent) was added, followed by ethyl chloroformate (1.51 ml., 1 equivalent). After 2 min. at −10°, H-Gly-Gly-OMe hydrochloride (2.88 g., 15.75 mM) was added, followed by N-methylmorpholine (1.73 ml., 1 equivalent). The mixture was stirred at −10° for 1 hr. and then allowed to warm up to ambient temperature over 2 hr. The solvent was evaporated in vacuo, the residue was dissolved in ethyl acetate (150 ml.), and the solution was washed successively with water (2×20 ml.), N-potassium carbonate (2×20 ml.) and water (2×20 ml.). The solution was dried (MgSO$_4$), filtered and evaporated in vacuo to give diallyl-Tyr(Bu$^t$)-Gly-Gly-OMe as an oil. The structure was confirmed by elemental analysis, mass spectroscopy and NMR.

The last-named compound (4.73 g., 10.6 mM) was dissolved in a mixture of methanol (25 ml.) and water (10 ml.), and 2N-aqueous sodium hydroxide (5.83 ml.) was added. After one hour the solvent was evaporated in vacuo, the residue was dissolved in water (10 ml.), and the solution was adjusted to pH 3 with N-aqueous hydrochloric acid. The oil which separated was extracted into ethyl acetate (2×50 ml.). The combined extracts were washed with water (2×20 ml.), dried (MgSO$_4$), filtered and evaporated in vacuo to give diallyl-Tyr(Bu$^t$)-Gly-Gly-OH as a foam.

C. [Diallyl-Tyr(Bu$^t$)-Gly-Gly-Phe-Leu-NH-CH$_2$-]$_2$

Diallyl-Tyr(Bu$^t$)-Gly-Gly-OH (see section B above; 0.75 g., 2 mM), (H-Phe-Leu-NH-CH$_2$-)$_2$ dihydrochloride (see section A above; 0.654 g. 1 mM), triethylamine (0.28 ml., 2 mM) and 1-hydroxybenzotriazole (0.27 g., 2 mM) were dissolved in DMF (20 ml.), and the solution was cooled to 0°. DCCI (0.412 g., 2 mM) was added and the mixture was stirred at 0° for 1 hr. and then at 4° for 24 hr. The mixture was filtered and the solvent was evaporated in vacuo. The residue was dissolved in ethyl acetate (100 ml.), and the solution was washed successively with 2N-potassium bicarbonate (4×20 ml.) and water (2×20 ml.). The solution was dried (MgSO$_4$), filtered and evaporated in vacuo. The crude product was purified on a column of silica gel (Kieselgel 60, Merck Art. 7734; 95 g.) which was equilibrated and eluted with chloroform and then with methanol/chloroform 1:19 v/v. The fractions which contained the pure product were combined and evaporated in vacuo to give [diallyl-Tyr(Bu$^t$)-Gly-Gly-Phe-Leu-NH-CH$_2$-]$_2$.

Example 2

[Diallyl-Tyr(Bu$^t$)-Gly-Gly-Phe-Leu-NH-(CH$_2$)$_4$-]$_2$ (1.15 g., 0.77 mM) was dissolved in TFA/water 9:1 v/v (25 ml.). The solution was kept at ambient temperature for 1 hr. The excess reagent was then evaporated in vacuo and the residue was dried in vacuo over potassium hydroxide. Trituration of the residue with diethyl ether gave a white solid which was collected by filtration and washed with diethyl ether. There was thus obtained [diallyl-Tyr-Gly-Gly-Phe-Leu-NH-(CH$_2$)$_4$-]$_2$ bis-trifluoroacetate, having $R_fK$ 0.69 and $R_fQ$ 0.3. The structure was confirmed by NMR.

The compound used as starting material was obtained by the same sequence of steps as described in Example 1, except that 1,8-diaminooctane was employed in place of 1,2-diaminoethane in section A.

EXAMPLE 3

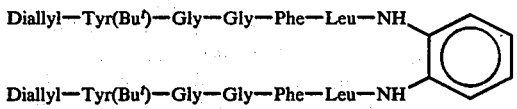

(1.4 g., 1 mM) was dissolved in TFA/water (25 ml.). The product was isolated as described in the preceding two Examples, and there was thus obtained:

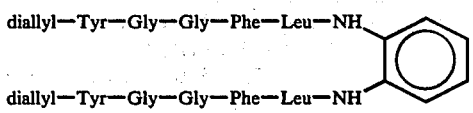

bis-trifluoroacetate, having $R_fP$ 0.1 and $R_fQ$ 0.4. The structure was confirmed by NMR.

The starting material was prepared by the same sequence of steps as described in Example 1, except that 1,2-diaminobenzene was used in place of 1,2-diaminoethane in section A, and the solvent used for the coupling reaction (Section A) was pyridine.

EXAMPLE 4

[Diallyl-Tyr(Bu$^t$)-Gly-Azgly-Phe-Leu-NH-CH$_2$-]$_2$ (0.34 g, 0.24 mM) was dissolved in TFA/water 9:1 v/v (5 ml.). The product was isolated as described in the preceding Examples, and there was thus obtained [diallyl -Tyr-Gly-Azgly-Phe-Leu-Nh-CH$_2$-]$_2$ having $R_fD$ 0.86 and $R_fQ$ 0.2. The structure was confirmed by NMR.

The starting material was obtained as follows:

A. (H-Leu-NH-CH$_2$-)$_2$.2HCl

BOC-Leu-OH.H$_2$O (24.9 g., 100 mM) was dissolved in DMF (30 ml.) and the solution was evaporated to dryness in vacuo. The procedure was repeated to ensure removal of water from the monohydrate, and the residue was then dissolved in DMF (200 ml.). N-methylmorpholine (11.2 ml., 1 equivalent) was added. The mixture was cooled to $-10°$ and ethyl chloroformate (9.6 ml., 1 equivalent) was added. After 2 min. at $-10°$, 1,2-diaminoethane (3.34 ml., 50 mM) were added and the mixture was stirred at $-10°$ for 1 hr. and at 4° for 16 hr. The mixture was poured into a mixture of water (200 ml.) and 1M-potassium hydrogen carbonate solution (200 ml.), and the resulting solid precipitate was collected by filtration, washed with water and dried in vacuo at 50°. There was thus obtained (BOC-Leu-NH-CH$_2$-)$_2$, the structure of which was confirmed by NMR.

The last-named compound (18.2 g., 39 mM) was dissolved in 3M-HCl in acetic acid (55 ml.). The solution was kept at ambient temperature for 1 hr. Dry ether (500 ml.) was added and the solid, (H-Leu-NH-CH$_2$-)$_2$.2HCl, was collected by filtration, washed with ether (100 ml.) and dried in vacuo over pellets of potassium hydroxide.

B. Z-Gly-Azgly-Phe-OH

H-Phe-OBu$^t$ (7.29 g., 33 mM) was dissolved in DMF (20 ml.) and the solution was cooled to 0°. N-Carbonyldiimidazole (5.35 g., 33 mM) was added and the mixture was stirred at 0° for 1 hr. Z-Gly-NH.NH$_2$ (7.35 g., 33 mM) was added and the mixture was stirred at 4° for 16 hr. The solvent was evaporated in vacuo and the residue was dissolved in ethyl acetate (200 ml.), washed with water (3×30 ml.) and dried (MgSO$_4$). The mixture was filtered and the solvent was evaporated to give impure Z-Gly-Azgly-Phe-OBu$^t$ as an oil. The last-named compound was dissolved in 6M-HCl in ethyl acetate (20 ml.) and the solution was kept at ambient temperature for 1 hr. The excess reagent was evaporated in vacuo, the residue was dissolved in ethanol/water 3:1 v/v (100 ml.), and the solution was passed slowly through a column of ion-exchange resin (AG1-X2, obtainable from Bio-Rad Laboratories, Richmond, Calif., U.S.A.; acetate form, 80 ml. wet resin). The column was washed with ethanol/water 3:1 v/v (500 ml.) and then with N-acetic acid in ethanol/water 3:1 v/v. (500 ml.). The acid eluate was evaporated in vacuo and the residue was triturated with water (50 ml.) to give a white solid which was collected by filtration and dried in vacuo over phosphorous pentoxide. There was thus obtained Z-Gly-Azgly-Phe-OH, the structure of which was confirmed by NMR.

C. [H-Gly-Azgly-Phe-Leu-NH-CH$_2$-]$_2$

Z-Gly-Azgly-Phe-OH (0.84 g., 2 mM), 1-hydroxybenzotriazole (0.23 g., 1.71 mM) and (H-Leu-NH-CH$_2$-)$_2$.2HCl (0.31 g., 0.86 mM) were dissolved in DMF (10 ml.), and the solution was stirred at 0°. DCCI (0.35 g., 1.71 mM) was added, followed immediately by triethylamine (0.24 ml., 1.71 mM). The mixture was stirred at 4° for 16 hr. and then filtered to remove the urea. The filtrate was evaporated in vacuo, the residue was triturated with 2N-potassium hydrogen carbonate solution (20 ml.), and the solid was collected by filtration, washed with water and dried in vacuo. There was thus obtained [Z-Gly-Azgly-Phe-Leu-NH-CH$_2$-]$_2$ contaminated by dicyclohexylurea and other trace impurities.

The last-named compound (0.71 g., 0.61 mM) was dissolved in DMF (60 ml.), and 5% palladium-on-carbon catalyst (0.3 g.) was added. The mixture was vigorously stirred and a slow stream of hydrogen was passed through it at ambient temperature for 3 hr. The catalyst was filtered off (kieselguhr), washed with DMF (10 ml.), and the solution was evaporated in vacuo to give crude (H-Gly-Azgly-Phe-Leu-NH-CH$_2$-)$_2$.

D. [Diallyl-Tyr(Bu$^t$)-Gly-Azgly-Phe-Leu-CH$_2$-]$_2$

Diallyl-Tyr(Bu$^t$)-OH (0.32 g., 1 mM) and N-methylmorpholine (0.112 ml., 1 mM) were dissolved in DMF (5 ml.), and the solution was cooled to $-10°$. Ethyl chloroformate (0.096 ml., 1 mM) was added and the mixture was stirred at $-10°$ for 2 min. (H-Gly-Azgly-Phe-Leu-NH-CH$_2$-)$_2$ (0.49 g., 0.6 mM) was then added, and the mixture was stirred at $-10°$ for 1 hr. and at 4° for 16 hr. The solvent was evaporated in vacuo and the residue was triturated with 2N-potassium hydrogen carbonate solution (20 ml.). The solid was collected by filtration, washed with water (10 ml.) and dried in vacuo over phosphorus pentoxide. The crude product was purified on a column of silica gel (Kieselgel 60, Merck Art. 7734; 95 g.) which was equilibrated and eluted with methanol/chloroform 1:19 v/v. The fractions which contained the pure product were combined and evaporated in vacuo to give [diallyl-Tyr(Bu$^t$)-Gly-Azgly-Phe-Leu-NH-CH$_2$-]$_2$, the structure of which was confirmed by NMR.

What we claim is:

1. A compound of the formula:

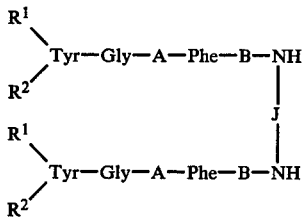

V wherein R$^1$ and R$^2$, which may be the same or different, stand for an alk-2-enyl radical of not more than 6 carbon atoms, A stands for Gly or Azgly, B stands for Leu or Met, and J stands for a group of the formula —(CH$_2$)$_n$—, wherein n stands for an integer from 1 to 10, or for a phenylene radical, or a pharmaceutically-acceptable acid-addition salt thereof.

2. A compound as claimed in claim 1 wherein R$^1$ and R$^2$ stand for an allyl or crotonyl radical.

3. A compound as claimed in claim 1 wherein n stands for 2, 4, 6 or 8.

4. A compound as claimed in claim 1 wherein J stands for an o-phenylene radical.

5. The compound claimed in claim 1 which is [diallyl-Tyr-Gly-Gly-Phe-Leu-NH-CH$_2$-]$_2$.

6. The compound claimed in claim 1 which is [diallyl-Tyr-Gly-Azgly-Phe-Leu-NH-CH$_2$-]$_2$.

7. A salt as claimed in claim 1 which is a salt derived from hydrochloric, phosphoric, acetic, citric or trifluoroacetic acid.

8. A pharmaceutical composition suitable for use as an opiate receptor antagonist comprising an effective amount of a compound of the formula V, wherein R$^1$, R$^2$, A, B and J have the meanings stated in claim 1, or a pharmaceutically-acceptable acid-addition salt thereof, and a pharmaceutically-acceptable diluent or carrier.

* * * * *